United States Patent [19]

Nakagawa et al.

[11] 4,126,696
[45] Nov. 21, 1978

[54] 4-ALKYLSULFONYLOXYPHENYL N-ALKYLTHIOLCARBAMATES AND USE THEREOF AS FUNGICIDE FOR AGRICULTURE

[75] Inventors: Taizo Nakagawa; Toshiyuki Suzuki, both of Ageo; Yutaka Watanabe, Saitama; Kaoru Ohmori, Okegawa; Iwao Tejima; Osamu Yamada, both of Ageo; Shuichi Ishida, Omiya, all of Japan

[73] Assignee: Nippon Kayaku Kabushiki Kaisha, Tokyo, Japan

[21] Appl. No.: 895,545

[22] Filed: Apr. 12, 1978

Related U.S. Application Data

[63] Continuation-in-part of Ser. No. 835,598, Sep. 22, 1977.

[30] Foreign Application Priority Data

Sep. 2, 1977 [JP] Japan .................................. 52-120362

[51] Int. Cl.$^2$ ...................... C07C 153/11; A01N 9/12
[52] U.S. Cl. ................................ 424/300; 260/455 A
[58] Field of Search .................... 260/455 A; 424/300

[56] References Cited

U.S. PATENT DOCUMENTS 3,932,632  1/1976  Adolphi et al. ...................... 424/300

Primary Examiner—Lewis Gotts
Assistant Examiner—Robert C. Whittenbaugh
Attorney, Agent, or Firm—Russell & Nields

[57] ABSTRACT

New 4-alkylsulfonyloxyphenyl N-alkylthiolcarbamates of the formula

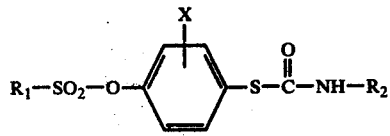

wherein each of $R_1$ and $R_2$ is a lower alkyl having from 1 to 6 carbon atoms and X is hydrogen, chlorine or methyl. The compounds have excellent effect on the prevention of the soil born plant diseases.

9 Claims, No Drawings

4-ALKYLSULFONYLOXYPHENYL N-ALKYLTHIOLCARBAMATES AND USE THEREOF AS FUNGICIDE FOR AGRICULTURE

This is a continuation-in-part of application Ser. No. 835,598 filed Sept. 22, 1977.

BACKGROUND OF THE INVENTION

It is well known that the prevention of the soil born plant diseases is very difficult. Except chlorobenzene derivatives such as sodium salt of the pentachlorophenol, the compounds developed as agricultural fungicides or industrial fungicide have little effect on the prevention of the said plant diseases.

The said chlorobenzene derivatives have a tendency to harm the plants and to polute the soil and water.

Therefore, the development of many new fungicides which have not the said undesirable tendency are proceeding for the prevention of the soil born plant diseases.

The compounds of the present invention have superior effect on the prevention of the soil born plant diseases and have not the said undesirable tendency. The compound of

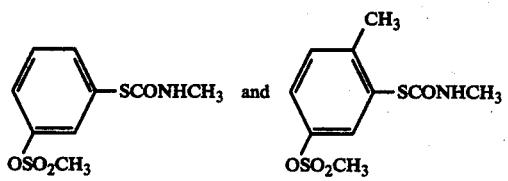

are disclosed as industrial fungicides in Japanese Laying-Open No. 135223/75.

These compounds have only inferior effect on the prevention of the soil born plant diseases though these compounds have very superior activity as an industrial fungicide.

SUMMARY OF THE INVENTION

The object of the present invention is to provide new 4-alkylsulfonyloxyphenyl N-alkylthiolcarbamates which exhibit superior effect on the prevention of the soil born plant diseases.

Another object of the present invention is to provide a fungicidal composition comprising said new 4-alkylsulfonyloxyphenyl N-alkylthiolcarbamates as an active ingredient and adjuvants.

Still another object of the present invention is to provide a method for preventing the soil born plant diseases comprising applying said new 4-alkylsulfonyloxyphenyl N-alkylthiolcarbamates to the soil which cultivate the plants or to seeds of plants.

DETAILED DESCRIPTION OF THE INVENTION

A compound of the present invention is represented by the following formula (I)

$$R_1-SO_2-O-\underset{X}{\bigcirc}-S-\overset{O}{\overset{\|}{C}}-NH-R_2$$

wherein each of $R_1$ and $R_2$ is a lower alkyl having from 1 to 6 carbon atoms preferably from 1 to 4 carbon atoms and X is hydrogen, chlorine or methyl.

The compounds of the present invention are prepared by the method A or B below.

Method A

Method A is illustrated by the following equation.

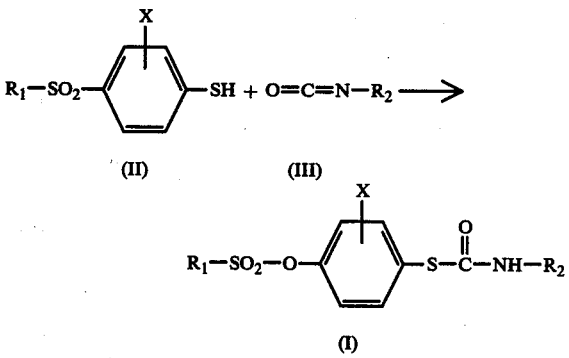

wherein $R_1$, $R_2$ and X are as described above.

The reaction of the benzenethiols of the formula (II) with the alkylisocyanates of the formula (III) is preferably conducted in an inert organic solvent in the presence of the catalyst such as triethylamine at the reaction temperature between room temperature and the boiling point of the inert organic solvent.

The preferred amount of the catalyst is 0.01–1% by weight of the benzenethiol of the formula (II). The benzenethiols of the formula (II) used as starting materials are obtained by the reduction of the corresponding benzenesulfonylchlorides according to the known method, for example, the method described in the Organic Synthesis Vol. 1, page 504. The benzenethiols are, for example, 4-methylsulfonyloxybenzenethiol (colorless transparent liquid, $n_D^{25}$ 1.5602), 3-chloro-4-methylsulfonyloxybenzenethiol (colorless transparent liquid $n_D^{25}$ 1.5861) and 3-methyl-4-methylsulfonyloxybenzenethiol (colorless transparent liquid, $n_D^{25}$ 1.5656).

The alkylisocyanates of the formula (III) are, for example, methylisocyanate, ethylisocyanate, propylisocyanate and buthylisocyanate. The inert organic solvents used the reaction are, for example, aliphatic and aromatic hydrocarbons and the derivatives substituted by halogen atoms thereof such as chloroform, tetrachloromethane, cyclohexane, toluene, xylene, benzene and chlorobenzene; ketones such as methylbutylketone and acetone; esters such as ethylacetate and butylacetate; aliphatic nitriles such as acetonitrile and propionylnitrile; ethers such as ethylether, tetrahydrofuran and dioxane.

Method B

Method B is illustrated by the following equation.

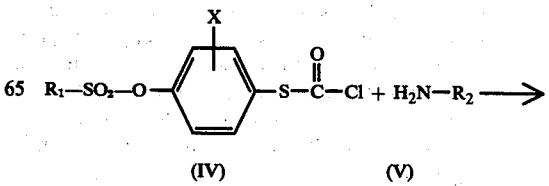

-continued the Table I were prepared by the method A or method B.

Table 1

| Compound Number | Formula | Melting point (° C) | The method of the preparation |
|---|---|---|---|
| No. 1 | CH$_3$SO$_2$—O—⟨C$_6$H$_4$⟩—S—C(=O)—NH·CH$_3$ | 127 – 120 | A |
| No. 2 | CH$_3$SO$_2$—O—⟨C$_6$H$_3$(Cl)⟩—S—C(=O)—NH·CH$_3$ | 91 – 91.5 | A |
| No. 3 | CH$_3$SO$_2$—O—⟨C$_6$H$_3$(H$_3$C)⟩—S—C(=O)—NH—CH$_3$ | 90 – 91 | A |
| No. 4 | CH$_3$SO$_2$—O—⟨C$_6$H$_4$⟩—S—C(=O)—NH·C$_2$H$_5$ | 87 – 88 | A |
| No. 5 | CH$_3$SO$_2$—O—⟨C$_6$H$_4$⟩—S—C(=O)—NH—C$_3$H$_7$(n) | 97.5 – 98 | B |
| No. 6 | CH$_3$SO$_2$—O—⟨C$_6$H$_4$⟩—S—C(=O)—NH—C$_4$H$_9$(n) | 100 – 101 | A |
| No. 7 | CH$_3$SO$_2$—O—⟨C$_6$H$_3$(H$_3$C)⟩—S—C(=O)—NH—C$_4$H$_9$(n) | 82 – 83 | A |
| No. 8 | C$_2$H$_5$SO$_2$—O—⟨C$_6$H$_4$⟩—S—C(=O)—NH·CH$_3$ | 82 – 83 | A |
| No. 9 | C$_2$H$_5$SO$_2$—O—⟨C$_6$H$_4$⟩—S—C(=O)—NH·C$_4$H$_9$(n) | 70 – 70.5 | A |

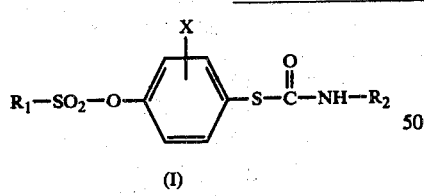

(I)

wherein R$_1$, R$_2$ and X are as described above.

This reaction is, usually, conducted in the inert organic solvent described in the Method A or in the mixture of the inert organic solvent and water. The preferred amounts of the amines of the formula (V) and the compound of the formula (IV) are in the molar ratio of 1–3 to 1. The reaction may be conducted in the presence of a base as a condensing agent, if necessary. The bases are, for example, an aliphatic, aromatic or hetarocyclic tertiary amine such as triethylamine, dimethylaniline and pyridine; carbonate and bicarbonate of an alkaline metal such as sodium carbonate, potassium carbonate and sodium bicarbonate; a strong base such as sodium hydroxide, potassium hydroxide and calicium hydroxide. The compounds of the present invention shown in the Table I were prepared by the method A or method B.

Compound No. 7 and the compounds of the formula (I) wherein each of R$_1$ and R$_2$ is methyl or ethyl (R$_1$ and R$_2$ may be the same groups or different groups) and X is hydrogen such as compound No. 1, No. 4 and No. 8 exhibit very excellent effect on the prevention of the soil born plant diseases and the most preferred compound is compound No. 1.

The preparation of the compounds of the present invention is more specifically illustrated in the following preparation examples.

Preparation Example 1 (Method A)

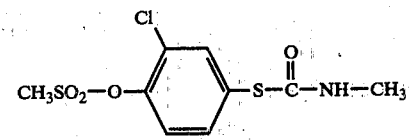

3-Chloro-4-methylsulfonyloxybenzenethiol (5.0 g; 0.021 mole) and methylisocyanate (1.3 g; 0.023 mole) were dissolved in benzene (20 cc).

A drop of triethylamine was added to the solution and the solution was left at room temperature for some time to obtain 3-chloro-4-methylsulfonyloxyphenyl-N-methyl thiolcarbamate.

The crude crystals obtained by condensing the resultant reaction mixture under the reduced pressure were recrystallized from a little amount of benzene to obtain white crystals (5.6 g; yield 90%).

Melting point: 91°–91.5° C.

Elemental analysis as $C_9H_{10}ClNO_4S$: Found C: 36.74%; H: 3.39%; N: 4.75%. Calculated C: 36.55%; H: 3.41%; N: 4.74%.

3-chloro-4-methylsulfonyloxybenzenethiol used as a starting material is prepared as follows:

The powdery zinc (255 g) was added to methanol (500 cc) and the mixture was stirred. 3-chloro-4-methylsulfonyloxybenzene sulfonylchloride (30.5 g; 0.10 mole) and 35% hydrochloric acid (83 cc) was added to the mixture, successively.

The resultant mixture was stirred and then the temperature of the mixture was elevated to 60°–70° C. 3-chloro-4-methylsulfonyloxy benzenesulfonylchloride (274.6 g; 0.90 mole) was added to the mixture little by little. After the addition was completed, 35% hydrochloric acid (743 cc) was added drop-wise to the resultant mixture under the said temperature and then the mixture was heated until the completion of the reaction. After the reaction was completed, the reaction mixture was added to the water and then extracted with benzene. The extract was washed with water two times and dried over anhydrous sodium sulfate and then the benzene was distilled away under the reduced pressure to obtain 186 g (yield: 78%) of colorless transparent liquid ($n_D^{25}$ 1.5861).

Said 3-chloro-4-methylsulfonyloxybenzene sulfonylchloride may easily be prepared by those skilled in the art as follows:

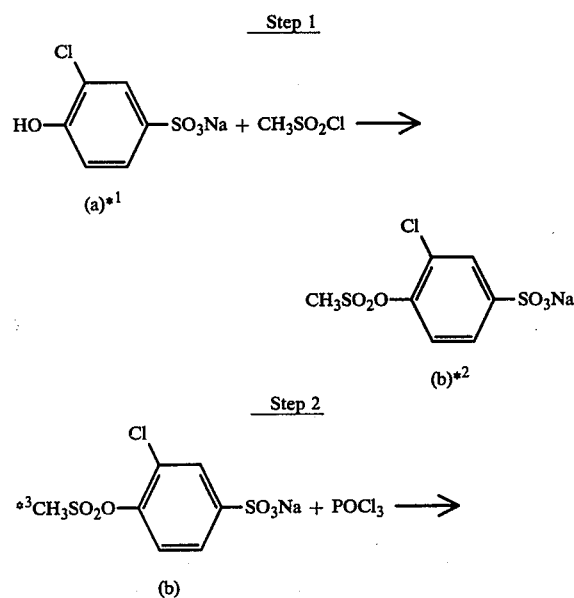

(b)

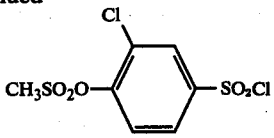

(c) 3-chloro-4-methyl-sulfonyloxybenzene sulfonylchloride

*Note 1:
3-chloro-4-hydroxybenzene sulfonic acid [compound (a)] is a known compound (see C.A. Vol. 54 14191b)
*Note 2:
Sodium salt of 3-chloro-4-methylsulfonyloxybenzene sulfonylchloride [compound (b)] is a new compound. However, it is known that methylsulfonyloxybenzenes are prepared by the reaction of phenols with methylsulfonylchlorides. (see Louis F. Fieser "Reagent for Organic Syntheses" P.664 or C.A. Vol.37, 50409)
*Note 3:
It is known that —SO₃Na group on benzene can be converted to —SO₂Cl with PCl₅ or POCl₃ (see Organic Syntheses Vol. 1, P.84 and C.A. Vol.82 (1975) 155756t)

Step 1 (the preparation of sodium salt of 3-chloro-4-methylsulfonyloxybenzene sulfonic acid) is carried out as follows:

Sodium hydroxide (109 g, 2.56 moles) and sodium salt of 3-chloro-4-hydroxy benzene sulfonic acid (492 g, 2.13 moles) were dissolved in water (100 cc). Methane sulfonylchloride (232 g, 2.03 moles) was added dropwise retaining the reaction temperature 5°–10° C. with cooling on an ice bath and stirring. After the completion of the addition, the ice bath was taken off and the reaction is continued for 2 hours with stirring. The resultant crystals were separated from the solution by filtration and dried. 453 g of the white crystals of sodium salt of 3-chloro-4-methylsulfonyloxybenzene sulfonic acid were obtained. Yield: 72.4%. Melting point: over 250° C.

Step 2 (the preparation of 3-chloro-4-methylsulfonyloxy benzene sulfonylchloride) is carried out as follows:

Sodium salt of 3-chloro-4-methylsulfonyloxybenzene sulfonic acid (453 g: 1.47 moles), N,N-dimethylformamide (21.1 g: 0.288 mole) and benzene (2000 cc) were mixed and heated with stirring until the mixture was refluxed. Phosphorus oxychloride (237 g: 1.55 moles) was added dropwise to the mixture for 1 hour. The resultant mixture was refluxed with stirring for an additional 3 hours and then water (1000 cc) was added to the resultant mixture under the temperature 20° C.–30° C. with cooling. The mixture was stirred for 1 hour under the same temperature and then the layer of benzene was separated from the mixture. The benzene solution separated was washed with water two times and dried over anhydrous sodium sulfate. Benzene was removed from the benzene solution by distillation to obtain crude white crystals (335. g) of 3-chloro-4-methylsulfonyloxybenzene sulfonylchloride. The crude white crystals were recrystalized from benzene. Yield: 74.7%. Melting point: 100°–100.5° C.

Preparation Example 2 (Method B)

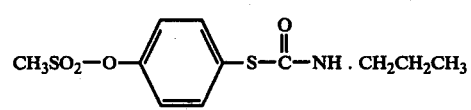

S-(4-methylsulfonyloxyphenyl) chlorothiocarbonate (8.0 g; 0.03 mole) was dissolved in benzene (50 cc). N-propylamine (3.9 g; 0.066 mole) was added drop-wise to the solution while maintaining the reaction temperature at 20°-25° C. with cooling and continuous stirring. After the addition, stirring was continued for another 2 hours. Water (100 cc) was added to the reaction mixture and then benzene layer was separated. The benzene solution separated was washed with 5% hydrochloric acid two times, with water two times and dried over anhydrous sodium sulfate. The benzene was distilled off to obtain the crude crystals. The crude crystals were recrystallzed from the mixture (the ratio of volume, 1:1) of cyclohexane and benzene to obtain the white crystals (5.3 g, yield 61.0%).

Melting point: 97.5°-98° C.

Elemental analysis as $C_{11}H_{15}NO_4S_2$; Found C: 45.50%; H: 5.19%; N: 4.94%. Calculated C: 45.66%; H: 5.22%; N: 4.84%.

The fungicidal compositions of the present invention comprise a bactericidally effective amount of the compound of the formula (1) and adjuvants.

The preferred fungicidal compositions comprise 1–95% by weight of the compound of the formula (I) and 99–5% by weight of said adjuvants. The most preferred fungicidal compositions comprise 2–90% by weight of the compound of the formula (I) and 98–10% by weight of adjuvants.

The fungicidal compositions can be solids such as dusts, granules or wettable powders; or they can be liquids such as emulsifiable concentrates.

The adjuvants used in the present invention include all the substances other than effective compounds, which substances are added so as to enhance, maintain and increase the effect of power of the active compound or to dilute the concentration of the active compound. The adjuvants are, for example, various kinds of carriers and surface active agents. The carriers in the form of solid are, for example, clay, kaolin, talc, diatomaceous earth, silica, calcium carbonate or the like.

The carriers in the form of liquid are benzene, alcohols, acetone, xylene, methylnaphthalene, cyclohexanone, dimethylformamide, dimethylsulfoxide, animal and vegetable oils, fatty acids and their esters, various kinds of surfactants, etc. It is also possible to enhance the effect by appropriately mixing the active compounds or the mixture of the compounds and carriers with auxiliary substances usually employed for agricultural preparations, such as an extending agent, an emulsifier, a wetting agent and a binding agent.

The present compounds may also be used in admixture with other agricultural fungicides, insecticides, herbicides, plant growth regulators, soil modifying agents or fertilizers.

The methods of the present invention for killing fungi which cause soil born plant diseases comprise applying to soil where plants are cultivated or to seeds of plants with a fungicidally effective amount of the compound of the formula (I).

When the compounds of the formula (I) are applied to soil for the soil treatment, preferably they are used in an amount of 0.05–10 kg/10 ares. When the compounds are applied to seeds of plants for seed treatment, the seeds are dipped into the diluted solution in which the compound is contained in an amount of about 0.05–1.0% or seeds are dressed with a dust in which the compound is contained. The amount of the compound dressed is 0.1–5% of seed weight. The representative plant diseases which are prevented by the application of the compound of the formula (I) are as follows:

(1) Soil treatment

Damping-off of cucumber, the name of a soil borne disease of cucumber, caused by the fungus *Pellicularia filamentosa*, fusarium wilt of cucumber caused by *Fusarium oxysporum f cucumerium*, southern blight of pepper caused by *Corticium rolfsii*, verticilium wilt of eggplant caused by *Verticillium albo-atrum*, club root of cabbage by *Plasmodiphora brassicae*, etc.

(2) Seed treatment

Seedling blight of rice plant caused by *Pellicularia filamentosa* and *Fusarium moniliforme*, cucumber scab caused by *Cladosporium cucumerinum*, damping-off of cucumber caused by *Pellicularia filamentosa*, etc.

The present invention will be explained more in detail by composition examples and experimental examples. Parts used in composition Examples are parts by weight.

Composition Example 1

| Dust | |
|---|---|
| Compound No. 6 | 5 parts |
| Clay | 95 parts |

The above ingredients are mixed and are ground until a homogeneous, freeflowing dust of the disired particle size is obtained. This dust is suitable for the soil treatment. Dust which contain a compound other than the compound No. 6 can be prepared by the same method with this example.

Composition Example 2

| Wettable Powder | |
|---|---|
| Compound No. 1 | 80 parts |
| Caolin | 15 parts |
| Sodium higher alkylsulfonate | 3 parts |
| Sodium ligninsulfonate | 2 parts |

The above ingredients are mixed and are ground until a wettable powder of disired particle size is obtained. This wettable powder is suspended into water and used for soil treatment. This wettable powder also can be used for seed dressing without dilution with water.

The wettable powder which contain a compound other than compound No. 1 as an active compound can be prepared by the same method with this example.

Composition Example 3

| Granules | |
|---|---|
| Compound No. 7 | 3 parts |
| Polyvinylalcohol | 2 parts |
| Clay | 95 parts |

The above ingredients are uniformly mixed and 15 parts of water are added.

The mixture is blended to become uniformly wet and formed into granules having a granules size of 0.7 mm by means of a granulating machine and the wet granules are dried to obtain dry granules.

Composition Example 4

Emulsifiable Concentrate

Compound No. 8 (20 parts) is dissolved into 60 parts of xylene. The mixture (15 parts) of the condensation product of alkylphenol and ethylene oxide is dissolved in the resultant solution to obtain an emulsifiable concentrate. This concentrate is diluted with water to form emulsion.

Composition Example 5

Micro-granules

Equal quantities of mixture of compound No. 4 and clay are previously crushed to pieces finely to form concentrated dusts.

93.5 parts of mineral micro-granule (74-210μ in diameter, non-oil-adsorptive) are taken into a suitable mixer, and 0.5 parts of binder "polyvinyl acetate" are added with a rotation, and the above concentrate dusts are added for covering to form micro-granules. The micro-granules of the compounds other than No. 4 are made similarly.

Experimental Example 1

Exterminating test on Fusarium wilt of cucumber

The pots (diameter 12 cm) are filled with field soil and then the soil is infected by adding 20 g of soil in which the pathogene (*Fusarium oxysporium f cucumerinum*) is cultivated. Thereafter, 18 seeds of cucumber (variety: Tokiwagibai) are sown in each pot. Eighty percent (80%) wettable powder of the present invention is diluted with water to obtain a suspension and each pot is drenched with the suspension in an amount of 100 milliliter.

Then, the pots are transferred into the greenhouse.

Fifty percent (50%) wettable powder of methyl-1-(butylcarbamoyl)-2-benzimidazolcarbamate on the market (control No. 1) and each 80%-wettable powder of 4-methylsulfonylphenyl-N-methylcarbamate (Control No. 2) and 4-ethylsulfonylphenyl-N-methylcarbamate (Control No. 3) prepared by the same method with the composition example 2 are used as controls and tested by the same method. After 2 weeks of the inoculation, degrees of attack by the pathogen are observed and a "Percentage of healthy seedlings" is calculated. The "Percentage of healthy seedlings" is calculated as follows:

$$\text{Percentage of healthy seedlings} = \frac{\text{Number of healthy seedlings in treated pot}}{\text{Number of germination in untreated and uninfected pot}} \times 100$$

The results are shown in Table 2.

Table 2

| Test compounds | Concentration | Percentage of healthy seedlings | Phytotoxicity |
|---|---|---|---|
| 1 | 500 ppm | 96.6 % | nil |
| 4 | 500 ppm | 82.8 % | nil |
| 5 | 500 ppm | 77.4 % | nil |
| 8 | 500 ppm | 96.5 % | nil |
| 12 | 500 ppm | 69.3 % | nil |
| Control No. 1 | 500 ppm | 45.0 % | nil |
| Control No. 2 | 500 ppm | 30.7 | nil |
| Control No. 3 | 500 ppm | 34.2 | nil |
| Inoculated and untreated | — | — | — |
| Non-inoculated and untreated | — | 100 | — |

Experimental Example 2

Exterminating test on phytophthora rot of cucumber

The pots (12 cm in diameter) are filled by field soil and then the soil is infected by adding 5 g of soil in which the pathogene (Phytophthora melonis) is cultivated. Each pot is added 0.2 g of 5%-dust of the present invention and the soil of 3 cm depth from the surface is mixed with the dust. Thereafter, 10 seeds of cucumber (variety; Ohyashima) are sown in each pot. Then, the pots are transferred into the greenhouse.

Four percent (4%) dust of 5-ethoxy-3-trichloromethyl-1,2,4-thiaziazol on the market (control No. 1) and 5% dust of 4-methylsulfonylphenyl-N-methyl carbamate (control No. 2) are used as controls and tested by the same method.

After 20 days of the inoculation, degrees of attack by the pathogen is observed and a "Percentage of healthy seedlings" was calculated as follows:

$$\text{Percentage of healthy seedlings} = \frac{\text{Number of healthy seedlings in treated pot}}{\text{Number of emerged seedlings in untreated and uninfected pot}}$$

The results are shown in Table 3.

Table 3

| Test compounds (Number) | Amount of treatment (Active ingredient) | Percentage of healthy seedlings | Phytotoxicity |
|---|---|---|---|
| 1 | 0.01 g/pot | 100 % | nil |
| 2 | 0.01 g/pot | 95 % | nil |
| 3 | 0.01 g/pot | 90 % | nil |
| 4 | 0.01 g/pot | 100 % | nil |
| 5 | 0.01 g/pot | 95 % | nil |
| 6 | 0.01 g/pot | 90 % | nil |
| 7 | 0.01 g/pot | 100 % | nil |
| 8 | 0.01 g/pot | 100 % | nil |
| 9 | 0.01 g/pot | 95 % | nil |
| Control No. 1 | 0.008 g/pot | 90 % | nil |
| Control No. 2 | 0.01 g/pot | 30 % | nil |
| Inoculated and untreated | — | — | — |
| Non-inoculated and untreated | — | 100 % | — |

Experimental Example 3

Exterminating test on seedling blight of rice plant

Nursery boxes (60 × 30 × 3 cm) are filled with soil and then the soil is infected by adding 200 g of the soil in which the pathogens (*Rhizopus oryzal* and *Fusarium roseum*) are cultivated. Ten grams (10 g) of five percent (5%) dust of the present invention are added into the each box and mixed with the soil.

Thereafter seeds of rice plant (variety: Nihonbare) are sowed in drills at a rate of 0.3 liter per box and grown up for 3 days in a moist chamber at 32° C., for 7 days in greenhouse and then for 14 days in the field.

As control, 4% dust of 3-hydroxy-5-methylisoxazol (Control No. 1) and 4% dust of tetrachloroisophtaronitrile (Control No. 2) are used and tested by the same method. After 24 days of inoculation degree of attack by the pathogen is observed and a "Percentage of healthy seedlings" was calculated as follows:

$$\text{Percentage of healthy seedlings} = \frac{\text{Number of healthy seedlings}}{\text{Number of observed seedlings}} \times 100$$

The results are shown in the Table 4.

Table 4.

| Test compounds (Number) | Amount of treatment (Active ingredient) | Percentage of healthy seedlings | Phytotoxicity |
|---|---|---|---|
| 1 | 0.5 g/box | 85.2 % | nil |
| 4 | 0.5 g/box | 83.2 % | nil |
| 5 | 0.5 g/box | 78.2 % | nil |
| 8 | 0.5 g/box | 81.5 % | nil |
| 9 | 0.5 g/box | 79.3 % | nil |
| Control No. 1 | 0.2 g/box | 74.2 % | nil |

Table 4.-continued

| Test compounds (Number) | Amount of treatment (Active ingredient) | Percentage of healthy seedlings | Phytotoxicity |
|---|---|---|---|
| Control No. 2 | 0.8 b/box | 74.2 % | nil |
| Untreated | — | 30.7 | — |

Experimental Example 4

Exterminating test on cucumber damping-off

The pots (12 cm diameter) are filled with field soil and inoculated uniformly with soil infested with *Rhizoctonia solani* in an amount of 5 g per pot.

Thereafter, ten seeds of cucumber (variety: Oyashima) are sown in each pot.

Eighty percent wettable powder of composition of the present invention is diluted with water to obtain a suspension and each pot is drenched with the suspension in an amount of 50 ml.

Then, the pots are transferred into the greenhouse, fifty percent (50%)-wettable powder of pentachloronitrobenzene on the market (Control) is used as control and tested by the same method. After 2 weeks of sowing, degrees of attack by the pathogen are observed and a "Percentage of healthy seedlings" is calculated. The "Percentage of healthy seedlings" is calculated as follows:

$$\text{Percentage of healthy seedlings} = \frac{\text{Number of healthy seedlings}}{\text{Number of germination in untreated and uninfected pot}} \times 100$$

The results are shown in Table 5

Table 5

| Test compounds | Concentration | Percentage of healthy seedlings | Phytotoxicity |
|---|---|---|---|
| 1 | 1,000 ppm | 80 % | nil |
| 2 | 1,000 ppm | 85 % | nil |
| 4 | 1,000 ppm | 90 % | nil |
| 5 | 1,000 ppm | 85 % | nil |
| 9 | 1,000 ppm | 80 % | nil |
| 10 | 1,000 ppm | 65 % | nil |
| 11 | 1,000 ppm | 60 % | nil |
| 13 | 1,000 ppm | 65 % | nil |
| Control | 1,000 ppm | 75 % | nil |
| Inoculated and untreated | — | — | — |
| Non-inoculated and untreated | — | 100 % | — |

Experimental Example 5

Exterminating test on chineese cabbage clubroot

The pots (15 cm in diameter) are filled with soils infected by *Plasmodiophora brassical* and mixed well with 5% dust of the composition of the present invention in an amount of 5 gram in each pot.

Thereafter, 15 seeds of chineese cabbage (variety: Taibyo 60 nichi) were sown in each pot.

Then, the pots are transferred to field.

Twenty percent (20%) dust of pentachloronitrobenzene on the market (Control) are used as control and tested by the same method. After 3 weeks of sowing, degrees of attack by the pathogen is observed and a "Percentage of healthy seedlings" is calculated as follows:

$$\text{Percentage of healthy seedlings} = \frac{\text{Number of healthy seedlings in each pot}}{\text{Number of observed seedlings in each pot}} \times 100$$

The results are shown in Table 6.

Table 6

| Test compound | Amount of treatment (Active Compound) | Percentage of healthy seedlings | Phytotoxicity |
|---|---|---|---|
| 1 | 0.25 g/pot | 100 % | nil |
| 2 | 0.25 g/pot | 93 % | nil |
| 3 | 0.25 g/pot | 100 % | nil |
| 4 | 0.25 g/pot | 100 % | nil |
| 5 | 0.25 g/pot | 90 % | nil |
| 6 | 0.25 g/pot | 87 % | nil |
| 7 | 0.25 g/pot | 100 % | nil |
| 8 | 0.25 g/pot | 100 % | nil |
| 9 | 0.25 g/pot | 96 % | nil |
| Control | 1 g/pot | 93 % | — |
| Untreated | — | — | — |

Experimental Example 6

Exterminating test for seed treatment

Cucumber seeds (variety: Oyashima) are dipped in the spores suspension of *Cladosporium cucumerinum* and dried. After 1 day, the seeds are dressed with 80% wettable powder of the present invention. On the other hand, other seeds are dipped in the solution of 80% wettable powder of the present invention. Five (5) seeds treated by either dressing or dipping are placed on each potato dextrose agar plate. After 10 days after the treatment, degree of attack by the pathogen are observed and the results are shown with an "Effective Index".

An "Effective Index" is calculated as follows:

$$\text{Effective index} = \frac{\text{Number of diseased seeds in untreated plate} - \text{Number of diseased seeds in treated plate}}{\text{Number of diseased seeds in untreated plate}} \times 100$$

The results are shown in Table 7.

Table 7

| Tested compounds (Number) | Method of treatment | Concentration (and dipped time) | Effective Index | Phytotoxicity |
|---|---|---|---|---|
| 1 | Dressed | 1 % | 94 | nil |
| 1 | Dipped | 5,000 ppm (30 min) | 87 | nil |
| 4 | Dressed | 1 % | 92 | nil |
| 4 | Dipped | 5,000 ppm (30 min) | 85 | nil |
| 7 | Dressed | 1 % | 89 | nil |
| 7 | Dipped | 5,000 ppm (30 min) | 85 | nil |

We claim:

1. A compound having the formula

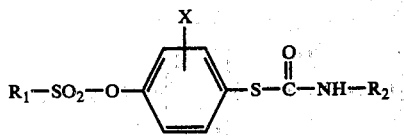

wherein each of $R_1$ and $R_2$ is a lower alkyl having from 1 to 6 carbon atoms and X is hydrogen, chlorine or methyl.

2. A compound as defined in claim 1 wherein each of $R_1$ and $R_2$ is methyl or ethyl and X is hydrogen.

3. A compound as defined in claim 1 wherein $R_1$ and $R_2$ are methyl and X is hydrogen.

4. A fungicidal composition comprising (1) from 1 to 95% by weight of a compound of the formula

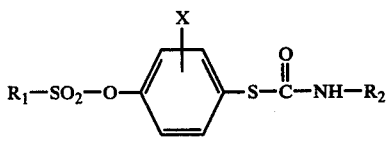

wherein each of $R_1$ and $R_2$ is a lower alkyl having from 1 to 6 carbon atoms and X is hydrogen, chlorine or methyl and (2) from 99% to 5% by weight of an adjuvant.

5. A fungicidal composition as defined in claim 4 wherein each of $R_1$ and $R_2$ is methyl or ethyl and X is hydrogen.

6. A fungicidal composition as defined in claim 4 wherein $R_1$ and $R_2$ are methyl and X is hydrogen.

7. A method for killing the fungi which harm plants comprising applying to soil or seeds of plants with an fungicidally effective amount of a compound of the formula

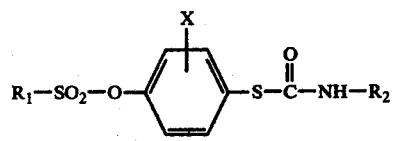

wherein each of $R_1$ and $R_2$ is a lower alkyl having from 1 to 6 carbon atoms and X is hydrogen chlorine or methyl.

8. A method as defined in claim 7 wherein each of $R_1$ and $R_2$ is methyl or ethyl and X is hydrogen.

9. A method as defined in claim 7 wherein $R_1$ and $R_2$ are methyl and X is hydrogen.

* * * * *